United States Patent
Pragl et al.

(10) Patent No.: US 11,446,381 B2
(45) Date of Patent: Sep. 20, 2022

(54) STABLE AQUEOUS FORMULATION FOR GROWTH HORMONE

(71) Applicant: SANDOZ AG, Basel (CH)

(72) Inventors: Bernt Pragl, Kundl (AT); Sabine Fuertinger, Kundl (AT)

(73) Assignee: SANDOZ AG, Basel (CH)

( * ) Notice: Subject to any disclaimer, the term of this patent is extended or adjusted under 35 U.S.C. 154(b) by 226 days.

(21) Appl. No.: 15/913,550

(22) Filed: Mar. 6, 2018

(65) Prior Publication Data

US 2018/0256722 A1 Sep. 13, 2018

Related U.S. Application Data

(63) Continuation of application No. 14/234,652, filed as application No. PCT/EP2012/064613 on Jul. 25, 2012, now abandoned.

(60) Provisional application No. 61/511,168, filed on Jul. 25, 2011.

(51) Int. Cl.
| | |
|---|---|
| *A61K 38/27* | (2006.01) |
| *A61K 47/02* | (2006.01) |
| *A61K 9/00* | (2006.01) |
| *A61K 9/08* | (2006.01) |

(52) U.S. Cl.
CPC ............ *A61K 47/02* (2013.01); *A61K 9/0019* (2013.01); *A61K 9/08* (2013.01); *A61K 38/27* (2013.01)

(58) Field of Classification Search
None
See application file for complete search history.

(56) References Cited

U.S. PATENT DOCUMENTS

| | | | |
|---|---|---|---|
| 5,763,394 | A | 6/1998 | O'Connor et al. |
| 6,448,225 | B2 | 9/2002 | O'Connor et al. |
| 6,593,296 | B1 | 7/2003 | McNamara et al. |
| 8,071,544 | B2 | 12/2011 | Chung et al. |

FOREIGN PATENT DOCUMENTS

| | | |
|---|---|---|
| WO | WO-01/03741 A1 | 1/2001 |
| WO | WO-2004/004780 A1 | 1/2004 |
| WO | WO-2004/082707 A2 | 9/2004 |
| WO | WO-2005/063298 A1 | 7/2005 |
| WO | WO-2005/105148 A2 | 11/2005 |
| WO | WO-2011/0060922 A1 | 5/2011 |

OTHER PUBLICATIONS

Nutropin AQ, package insert, Genentech, pp. 1-25, 2008.*
U.S. Appl. No. 14/234,652 (2014/0194356), filed Mar. 5, 2014 (Jul. 10, 2014), Pragl et al. (Sandoz AG).
Banga, A.K., Therapeutic Peptides and Proteins: Formulation, Processing, and Delivery Systems (2nd Edition), Boca Raton, FL, USA, CRC Press, 2005, pp. 91-98.
Chi, E.Y. et al., Physical Stability of Proteins in Aqueous Solution: Mechanism and Driving Forces in Nonnative Protein Aggregation. Pharmaceut Res. 2003; 20(9):1325-36.
UniProt Database Accession No. P01241 "Soma Human."
International Search Report dated Oct. 22, 2012 by the International Searching Authority for PCT/EP2012/064613, which was filed on Jul. 25, 2012 and published as WO 2013/014196 on Jan. 31, 2013 (Inventor—Pragl et al.; Applicant—Sandoz AG) (5 pages).
Notice of Reasons for Rejection dated Mar. 29, 2016 by the Japanese Patent Office for Patent Application No. 2014-522080, which was filed on Jul. 25, 2012 and published as JP 2014-528919 on Oct. 30, 2014 (Inventor—Pragl et al.; Applicant—Sandoz AG) (Original—5 pages // Translation—8 pages).
Decision of Rejection dated Jan. 10, 2017 by the Japanese Patent Office for Patent Application No. 2014-522080, which was filed on Jul. 25, 2012 and published as JP 2014-528919 on Oct. 30, 2014 (Inventor—Pragl et al.; Applicant—Sandoz AG) (Original—5 pages // Translation—7 pages).
Office Action dated Feb. 27, 2018 by the Japanese Patent Office for Patent Application No. 2014-522080, which was filed on Jul. 25, 2012 and published as JP 2014-528919 on Oct. 30, 2014 (Inventor—Pragl et al.; Applicant—Sandoz AG) (Original—4 pages // Translation—6 pages).

* cited by examiner

*Primary Examiner* — Christine J Saoud
(74) *Attorney, Agent, or Firm* — Ballard Spahr LLP (57) ABSTRACT

The present invention is related to a pharmaceutically acceptable aqueous formulation comprising at least a neutral salt and a biopharmaceutical protein, wherein the concentration ratio between the biopharmaceutical protein and the neutral salt is in the range of ≥0.7 and ≤5.

20 Claims, 4 Drawing Sheets

STABLE AQUEOUS FORMULATION FOR GROWTH HORMONE

CROSS-REFERENCE TO RELATED APPLICATIONS

This Application is a Continuation of U.S. application Ser. No. 14/234,652, filed on Mar. 5, 2014, which is a national stage filing under 35 U.S.C. § 371 of International Application No. PCT/EP2012/064613, filed on Jul. 25, 2012, which claims the benefit of U.S. Provisional Application No. 61/511,168, filed on Jul. 25, 2011, the contents of which are incorporated herein by reference in their entireties.

BACKGROUND

In the recent years, biopharmaceutical drugs have entered the market, particularly protein drugs, both isolated from biological resources and/or produced with recombinant means.

The successful use of such biopharmaceuticals as therapeutics requires the preservation of their biological activity in all steps of development including storage and delivery. Compared to conventional small molcecular drugs, proteins pose additional challenges in preserving their activity because they are much larger, contain relatively labile groups, possess fragile 20 three-dimensional structures, and can furthermore be subject to metabolic processes, e.g., by microorganismic contaminations.

Degradation may occur in different ways, including aggregation of molecules, denaturation of tertiary structure, and deamidation of amino acid residues, e.g., asparagine and glutamine with their amide-containing side chains. Generally, all these processes of degradation are accelerated under suboptimal storage conditions, e.g., raised temperature, exposure to light, and/or high relative humidity.

Aggregation can take place in the form of visible aggregates and sub visible aggregates. Once formed, however, the latter can act as aggregation seeds for the formation of larger (then visible) aggregations.

These problems are even aggravated in the case of a biopharmaceutic provided in an aqueous formulation. Such a ready-to-use formulation is, however, commonplace because of ease and safety of administration, for example, for monoclonal antibodies as well as for smaller biopharmaceutics such as insulin, erythropoietin, or human Growth Hormone.

Due to the fact that the production of biopharmaceutics is a highly complex matter, production facilities are concentrated in particular clusters where the respective expertise exists. These facilities are not as evenly distributed, geographically, as, for example, facilities for the production of small molecular drugs. Further, because manufacturing capacities are in short supply, the production of a given drug often takes place in a relatively large batch and then another drug steps in.

For these reasons, biopharmaceutical drugs are often produced to stock, and are thus subject to relatively long periods of storage times and/or have to undergo long transportation routes before they reach the point of care. This situation is even worsened by the fact that in many cases it cannot be guaranteed that the cooling chain remains unbroken during storage and/or transport.

Under these conditions, the risk increases that biopharmaceutics reach the point of care in a state of advanced degradation, and can thus need to be discarded, which involves substantial financial losses, e.g., for the healthcare sponsoring institutions due to the relatively high market prices for biopharmaceutics, and may, in the worst case, isolate a patient from an essential treatment.

It is, thus, an object of the present invention to provide formulations and methods that help to overcome the above-mentioned problems.

SUMMARY OF THE INVENTION

Before the invention is described in detail, it is to be understood that this invention is not limited to the particular component parts of the devices described or process steps of the methods described, as such devices and methods may vary. It is also to be understood that the terminology used herein is for purposes of describing particular embodiments only, and is not intended to be limiting. It must be noted that, as used in the specification and the appended claims, the singular forms "a," "an," and "the" include singular and/or plural referents unless the context clearly dictates otherwise. It is, moreover, to be understood that, when parameter ranges are given that are delimited by numeric values, the ranges are deemed to include these limitation values.

According to one aspect of the invention, disclosed is a pharmaceutically acceptable aqueous formulation comprising at least a neutral salt and a biopharmaceutical protein, wherein the concentration ratio between the biopharmaceutical protein and the neutral salt is in the range of ≥0.7 and ≤5.

As used herein, the term "biopharmaceutical protein" relates to physiologically active proteins both isolated from biological resources and/or produced with recombinant means.

As used herein, the term "concentration" refers to the weight of a given substance per volume, i.e., to weight concentration. For example, the concentration of a biopharmaceutic is provided in a concentration of $mg\ ml^{-1}$.

It is important to say that the weight of the biopharmaceutical protein refers to weight of the protein alone, i.e, to the one or more amino acid chains which constitute the protein, plus, if applicable, the one or more glycosylation patterns. In case the protein is provided in a delivery system, or pegylated, or modified elsehow, the weight does not include said modifications, which can add substantial additional weight.

As used herein, the term "concentration ratio" refers to the dimensionless ratio of the concentrations of at least two substances. For example, if the biopharmaceutic is provided in a concentration of $10\ mg\ ml^{-1}$ and the neutral salt is provided in a concentration of $7.07\ mg\ ml^{-1}$, the resulting concentration ratio between the biopharmaceutical protein and the neutral salt would be 10/7.07=1.416.

The inventors have for the first time shown that in an aqueous formulation comprising biopharmaceutical aggregations, particularly sub-visible aggregations can be reduced in cases where said particular concentration ratio between the biopharmaceutic and the neutral salt is provided.

Preferably, said concentration ratio is 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

According to a preferred embodiment, the biopharmaceutical protein has between ≥15 and ≤220 amino acid residues and/or a molecular weight between ≥15 and ≤26 kDaltons.

Preferably, the protein has 150, 151, 152, 153, 154, 155, 156, 157, 158, 159, 160, 1641, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, or 220 amino acid residues; and/or a molecular weight of 15, 16, 17, 18, 19, 20, 21, 22, 23, 24, 25, or 26 kDaltons.

According to another preferred embodiment, the biopharmaceutical protein is human growth hormone (hGH). Human Growth Hormone (hGH) is a protein-based peptide hormone which stimulates growth, cell reproduction, and regeneration in humans and other animals. hGH is a single-chain polypeptide that is synthesized, stored, and secreted by the somatotroph cells within the lateral wings of the anterior pituitary gland. hGH is primarily used to treat children's growth disorders and adult growth hormone deficiency. Prior to its production by recombinant DNA technology, growth hormone was extracted from human pituitary glands (Cadaver growth hormone, also referred to as NPA growth hormone). Today, hGH is primarily produced with recombinant DNA technology (rhGH, also referred to as somatropin). rhGH has, typically, 191 amino acid residues. The amino acid sequence is available in the UniProt Database under accession No. P01241. Another variant is met-GH ("methionyl-growth hormone"), which has the same amino acid sequence as hGH, with an extra N-terminal methionine.

In the context of the present invention, the term human growth hormone (hGH) encompasses all the above-mentioned variants.

According to another preferred embodiment, the formulation further comprises at least one agent selected from the group consisting of:
 a buffer;
 a non-ionic surfactant;
 a tonifier; and/or
 a preservative.

Preferably, said buffer is selected from the group consisting of:
 Phosphate buffer ($Na_3PO_4$, $NaH_2PO_4$ and/or $Na_2HPO_4$);
 Citrate;
 Tris;
 Succinate;
 Acetate; and/or
 Histidine.

According to another preferred embodiment, said non-ionic surfactant is selected from the group consisting of:
 Poloxamer, preferably Poloxamer 188 or Poloxamer 184; Pluronic F-68; and/or
 Polysorbate, preferably Polysorbate 20 or Polysorbate 80.

The term "tonifier," as used herein, relates to an osmotically active substance that can be used to affect the osmolarity of a pharmaceutical formulation. According to another preferred embodiment, said tonifier is selected from the group consisting of:
 Mannitol;
 Glycine; and/or
 Sorbitol.

According to another preferred embodiment, said preservative is selected from the group consisting of:
 Phenol;
 meta-cresol;
 methyl paraben;
 propyl paraben;
 benzalconium chloride;
 benzethonium chloride; and/or
 benzyl alcohol.

Suitable concentrations for the buffers, non-ionic surfactants, tonifiers, and/or preservatives are, for example, shown in Table 2.

According to another preferred embodiment of the formulation according to the invention, human growth hormone (hGH) is present in a concentration ranging between $\geq 3$ and $\leq 20$ mg ml$^{-1}$.

Preferably, hGH is present in a concentration of 3, 3.33, 4, 5, 6, 7, 8, 9, 10, 11, 12, 13, 14, 15, 16, 17, 18, 19, or 20 mg ml$^{-1}$.

Particularly preferred concentrations for hGH are, for example, shown in Table 2.

According to another preferred embodiment of the formulation according to the invention, said neutral salt is selected from the group consisting of:
 Sodium Chloride (NaCl).

Preferably, said neutral salt is present in a concentration ranging between $\geq 2$ and $\leq 100$ mg ml$^{-1}$. Preferably, said neutral salt is present in a concentration of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg ml$^{-1}$.

Particularly preferred concentrations for the neutral salt are, for example, shown in Table 2. According to another preferred embodiment of the formulation according to the invention, the pH of said formulation is in a range between $\geq 5.8$ and $\leq 6.2$. Preferably, said pH is 5.8, 5.9, 6.0, 6.1, or 6.2. Particularly preferred pH values are, for example, shown in Table 2.

The formulation according to the invention has an optimized stability. Said optimized stability results, e.g., in reduced formation of visible and subvisible aggregates, reduced formation of precipitates, and reduced tendency to develop turbidity, particularly after long storage or storage under suboptimal conditions.

This feature is particularly beneficial under conditions where it cannot be guaranteed that the cooling chain remains unbroken, as can, for example, be the case in emerging markets and/or developing countries.

The formation of aggregates can, for example, be analyzed with light obscuration particle counting, size exclusion HPLC (SE-HPLC), and/or dynamic light scattering (DLS).

Light obscuration particle counting (LOPC) is a method that helps to detect and count particles. The nature of particle counting is based upon either light scattering or light obscuration. A high energy light source is used to illuminate the particle as it passes through the detection chamber. The particle passes through the light source (typically a laser) and if light scattering is used, then the redirected light is detected by a photo detector, whereas, if light obscuration is used, the loss of light is detected. The amplitude of the resulting signal represents the amount of the light scattered or light blocked.

Size exclusion HPLC (SE-HPLC) separates particles on the basis of size. It works by trapping smaller molecules in the pores of gel particles. The larger molecules simply pass by the pores as they are too large to enter the pores. Larger molecules, therefore, flow through the column quicker than smaller molecules; that is, the smaller the molecule, the longer the retention time. SE-HPLC is often used to provide quantitative analysis of protein aggregates and clips, and thus plays an important role in quality control of biopharmaceuticals.

Dynamic light scattering (DLS) is a technique in physics, which can be used to determine the size distribution profile of small particles in suspension or polymers in solution. It can also be used to probe the behavior of complex fluids such as concentrated polymer solutions.

When light hits small particles the light scatters in all directions (Rayleigh scattering) so long as the particles are small compared to the wavelength (below 250 nm). If the light source is a laser, and, thus, is monochromatic and coherent, then one observes a time-dependent fluctuation in the scattering intensity. These fluctuations are due to the fact that the small molecules in solutions are undergoing Brownian motion and so the distance between the scatterers in the solution is constantly changing with time. This scattered light then undergoes either constructive or destructive interference by the surrounding particles and within this intensity fluctuation, information is contained about the time scale of movement of the scatterers. Sample preparation either by filtration or centrifugation is critical to remove dust and artifacts from the solution.

It is noteworthy to mention that, while SE HPLC is a standard method for quality control in Biopharmaceutics, DLS and LOPC have a better resolution, i.e., they can detect even sub-visible aggregates that cannot be detected with SE HPLC. The present study is the first that makes use of DLS and LOPC for the screening of different formulations for Biopharmaceutics.

Accordingly, in this study it has for the first time been shown that aggregations, particularly sub-visible aggregations (which remained undetected in case SE HPLC was used) can be reduced in case a particular ratio between a biopharmaceutic and a neutral salt is provided.

According to another aspect of the invention, a method of increasing the stability of a pharmaceutically acceptable aqueous formulation comprising a biopharmaceutical protein is provided. Said method comprises providing the biopharmaceutical protein and the neutral salt in a final concentration ratio in the range of ≥0.7 and ≤5.

According to a preferred embodiment, the biopharmaceutical protein is human growth hormone (hGH).

Other preferred embodiments of said method can be derived from the above description related to preferred embodiments of the formulation according to the invention.

According to another aspect of the invention, the use of a formulation according to the invention is for the treatment of at least one condition selected from the group consisting of:
Growth Hormone Deficiency;
small for gestational age (SGA) or intrauterine growth retardation (IUGR);
Idiopathic Short Stature;
AIDS Wasting and Cachexia;
Short Stature Caused by Turner's Syndrome;
Short Stature Caused by Prader-Willi Syndrome;
Growth Problems Caused by Short Bowel Syndrome;
Improper Growth in Children with Renal Disease;
Rheumatoid Arthritis;
Osteoporosis;
X-Linked Hypophosphatemia Rickets.

According to another aspect of the invention, a primary packaging comprising the formulation according to the invention is provided. Said primary packaging is preferably a vial, a pre-filled syringe, a carpule, a bottle, or a cartridge.

In Table 1, different aqueous formulations from the prior art (comprising sodium chloride as a neutral salt and human growth hormone as the biopharmaceutical) used in the formulation according to the invention are shown. In all cases, the concentration ratio between the biopharmaceutical protein and the neutral salt is smaller than 0.7.

In Table 2, different formulations which have been developed under the gist of the present invention are shown.

Table 3 shows other aqueous formulations from the prior art comprising human growth hormone, but without a neutral salt.

TABLE 1

| | | Formulations from the prior art comprising a neutral salt | | | | | | | | |
|---|---|---|---|---|---|---|---|---|---|---|
| | | Accretropin ® | Nutropin ® | WO0103741 (Grandis) | | | | | | |
| Component | Role | (Cangene) | (Genentech) | I | III | Form. A | Form. B | Form. C | Form. D | Form. E |
| Volume | | 1 ml | 2 ml | 1 ml | 1 ml | 1 ml | 1 ml | 1 ml | 1 ml | 1 ml |
| hGH | active ingredient | 5 mg | 10 mg | 3.33 mg | 3.33 mg | 3.33 mg | 3.33 mg | 3.33 mg | 3.33 mg | 3.33 mg |
| Phosphate | buffer | 10 mM | | | | 10 mM | 10 mM | | 10 mM | |
| Citrate | | | 10 mM | | | | | 10 mM | | 10 mM |
| $NaH_2PO_4$ | | | | 1.05 mg | 1.05 mg | | | | | |
| $Na_2HPO_4$ | | | | 0.17 mg | 0.17 mg | | | | | |
| pH | | 6 | | 6 | 6 | 5.6 | 5.6 | 5.6 | 6 | 6 |
| Poloxamer 188 | non ionic surfactant | 2 mg | | | | | | | | |
| Pluronic F-68 | | | | | | 0.8 mg | | 0.8 mg | | 0.8 mg |
| Polysorbate 20 | | | 4 mg | | | | | | | |
| Phenol | preservative | 3.4 mg | 5 mg | | | | | | | |
| Benzyl Alcohol | | | | | | 9 mg | 9 mg | 9 mg | 9 mg | 9 mg |
| Mannitol | tonifier | | | | | | | | | |
| Glycine | | | | | | | | | | |
| NaCl | neutral salt | 7.5 mg | 17.4 mg | 5.85 mg | 5.85 mg | 5.9 mg | 5.9 mg | 5.9 mg | 5.9 mg | 5.9 mg |
| conc ratio hGH/NaCl | | 0.667 | 0.574 | 0.569 | 0.569 | 0.564 | 0.564 | 0.564 | 0.564 | 0.564 |

TABLE 2

*exemplary, non-restricting formulations according to the invention*

| Component | Role | per cartridge (1.5 [[1.5]] ml) | | | 0831RS156_5 | 0835RS158_5 | 0835RS158_6 | 0835RS158_7 | 0821RS148_5 |
|---|---|---|---|---|---|---|---|---|---|
| Volume | | 1.5 ml | 1.5 ml | 1.5 ml | 1 ml | 1 ml | 1 ml | 1 ml | 1 ml |
| hGH | active ingredient | 5 mg | 10 mg | 15 mg | 10 mg | 10 mg | 10 mg | 10 mg | 10 mg |
| Phosphate Citrate NaH2PO4 Na2HPO4 | buffer | 10 mM | 10 mM | 10 mM | 10 mM | 10 mM | 10 mM | 10 mM | 10 mM |
| pH | | 6.1 | 6.1 | 6.1 | 6.12 | 6.12 | 6.12 | 6.12 | 6.12 |
| Poloxamer 188 Pluronic F-68 Polysorbate 20 | non ionic surfactant | 3 mg | 3 mg | 4.5 mg | 2 mg | 3 mg | 3 mg | 3 mg | 2 mg |
| Phenol | preservative | | 4.5 mg | 4.5 mg | 3 mg | 3 mg | 3 mg | 3 mg | 3 mg |
| Benzyl Alcohol | | 13.5 mg | | | | | | | |
| Mannitol | tonifier | 51.5 mg | | | | 22.3 mg | | | |
| Glycine | | | 27.75 mg | | | | | | |
| NaCl | neutral salt | 3.5 mg | 7 mg | 10.5 mg | 7.07 mg | 3.5 mg | 7.07 mg | 14 mg | 7.07 mg |
| conc ratio hGH/NaCl | | 2.86 | 1.43 | 1.43 | 1.416 | 2.86 | 1.41 | 0.71 | 1.4116 |

TABLE 3

*Formulations from the prior art without a neutral salt*

| Component | Role | Protropin (Genentech) | Humatrope (Eli Lilly) | Norditropin SimpleXx (Novo Nordisk) | | | WO9403198 (Genentech) experimental example | reference | WO0103741 (Grandis) II | IV | V | VI |
|---|---|---|---|---|---|---|---|---|---|---|---|---|
| Volume | | per vial | per vial | 1.5 ml | 1.5 ml | 1.5 ml | 1 ml | 1 ml | 1 ml | 1 ml | 1 ml | 1 ml |
| hGH | active ingredient | | 5 mg | 5 mg | 10 mg | 15 mg | 5.0 mg | 5.0 mg | 3.33 mg | 3.33 mg | 3.33 mg | 3.33 mg |
| Phosphate buffer | | | | | | | | 1.7 mg | | | | |
| NaH2PO4 | | 0.1 mg | | | | | | | 1.05 mg | 1.05 mg | 1.05 mg | 0.85 mg |
| Na2HPO4 | | 1.6 mg | 1.13 mg | | | | | | 0.17 mg | 0.17 mg | 0.17 mg | 0.31 mg |
| Histidine | | | | 1 mg | 1 mg | 1.7 mg | | | | | | |
| pH | | 7.8 | 7.5 | | | | 6 | | 6 | 6 | 6 | 6.2 |
| Poloxamer 188 | non ionic surfactant | | | 4.5 mg | 4.5 mg | 4.5 mg | | | | | | |
| Pluronic F-68 | | | | | | | | | | | 2 mg | 2 mg |
| Polysorbate 20 | | | | | | | | 2 mg | | | | |
| Phenol | preservative | | | 4.5 mg | 4.5 mg | 4.5 mg | 2.5 mg | | | | | |
| Benzyl Alcohol | | | | | | | | 9 mg | 9 mg | 9 mg | 9 mg | |
| Mannitol | tonifier | 40 mg | 25 mg | 60 mg | 60 mg | 58 mg | | 45 mg | | | 35 mg | 35 mg |
| Glycine | | | 5 mg | | | | | 1.7 mg | | | | |
| NaCl | neutral salt | | | | | | | | | | | |

BRIEF DESCRIPTION OF THE EXAMPLES AND DRAWINGS

Additional details, features, characteristics, and advantages of the object of the invention are disclosed in the sub-claims, and the following description of the respective figures and 5 examples, which, in an exemplary fashion, show preferred embodiments of the present invention. However, these drawings should by no means be understood as to limit the scope of the invention.

Example 1: Tonifier Screening

Six formulation development batches (no tonifier, Glycine, Mannitol, Sorbitol, and NaCl) were compared. Batches comprising 15 mg hGH in aqueous solution (10.0 mg/ml, solution for injection 1.5 ml cartridge) were stored for 18 months at 5° C.±3° C. ("intended storage condition"), 3 months at 25° C.±2° C./60% relative humidity ("accelerated storage condition") and 2 weeks at 40° C.±2° C. ("stressed storage condition"). The different formulations are shown in table 4.

TABLE 4

| | Formulation No | | | | | |
|---|---|---|---|---|---|---|
| | 0821RS148_1 | 0821RS148_2 | 0821RS148_3 | 0821RS148_4 | 0821RS148_5 | 0821RS148_6 |
| hGH | 10 mg/ml | 10 mg/ml | 10 mg/ml | 10 mg/ml | 10 mg/ml | 10 mg/ml |
| Phosphate | 10 mM | 10 mM | 10 mM | 10 mM | 10 mM | 10 mM |
| Glycine | | 18.17 mg/ml | | | | |
| Mannitol | | | 44.09 mg/ml | | | 44.09 |
| Sorbitol | | | | 44.09 mg/ml | | |
| NaCl | | | | | 7.07 mg/ml | |
| Poloxamer 188 | 2 mg/ml | 2 mg/ml | 2 mg/ml | 2 mg/ml | 2 mg/ml | 3 mg/ml |
| Phenol | 3 mg/ml | 3 mg/ml | 3 mg/ml | 3 mg/ml | 3 mg/ml | 3 mg/ml |
| pH | 6.12 | 6.12 | 6.12 | 6.12 | 6.12 | 6.12 |
| water ad | 1 ml | 1 ml | 1 ml | 1 ml | 1 ml | 1 ml |
| tonicity | | 300 | 300 | 300 | 300 | 300 |

All tested batches appeared as a clear and colorless solution at the initial time point. During storage at 25° C. all formulations except #0821RS148-5 (see table 4) containing NaCl turned turbid or opalescent. After 2 months of storage at 5° C.±3° C. formulations containing Mannitol and Sorbitol turned progressively turbid/opalescent while formulation #082IRS 148-containing NaCl stayed clear over the whole storage period. All observations are backed by particle counting and DLS data. Notably, all aggregation processes could not be monitored by SE-HPLC. At accelerated conditions it was observed a marginal increase in aggregation by SE-HPLC. During storage at 25° C. all formulations except #082IRS148-5 containing NaCl turned turbid or opalescent. At stressed conditions a slight increase in aggregation was observed by SE-HPLC. During storage at 40° C. all formulations are clear.

Figure 1:
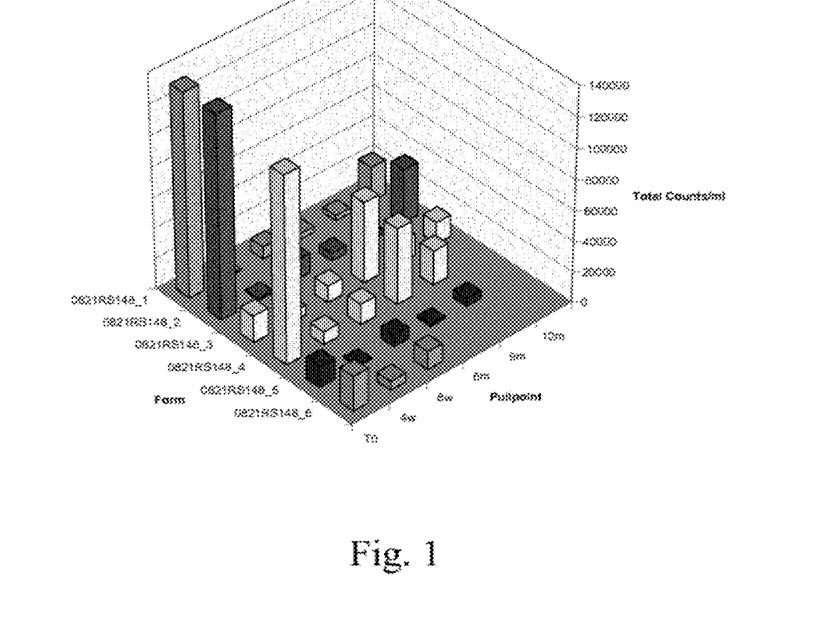
FIG. 1: Particle distribution of samples stored at 5° C. in the first tonifier screening experiment (example 1, "intended storage condition"), as determined with light obscuration Particle Counting, is shown. In general, sub-visible particle levels were high at the initial time point and show elevated levels for formulations containing no tonifier, Glycine, Mannitol, and Sorbitol. NaCl containing formulations showed the lowest sub-visible particle levels. These findings are further backed by DLS data and appearance data.
Figure 2:
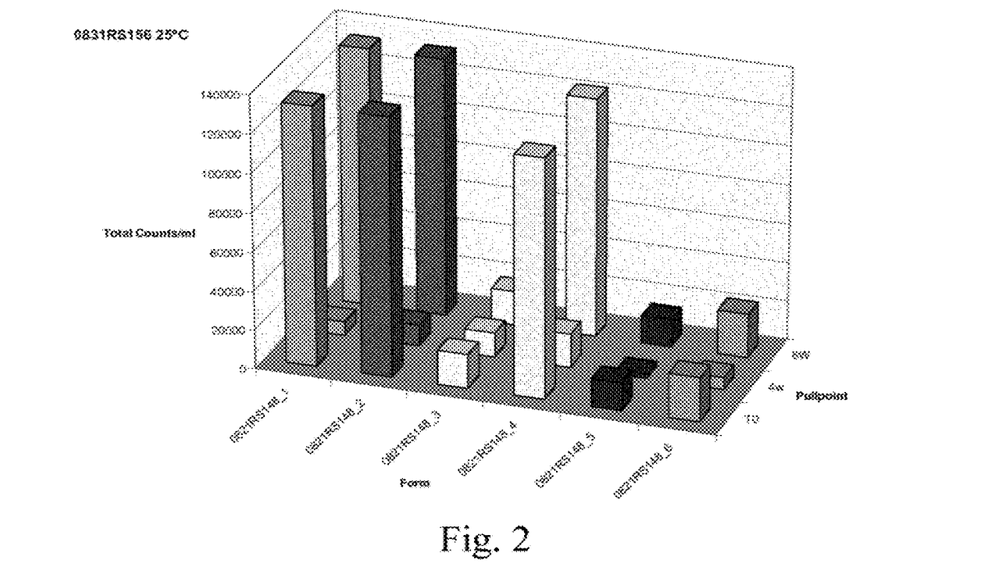
FIG. 2: Particle distribution of samples stored at 25° C. in the first tonifier screening experiment 25 (example 1, "accelerated storage condition"), as determined with light obscuration Particle Counting, is shown. In general, sub-visible particle levels were high at the initial time point but stayed at elevated levels for formulations containing no tonifier, Glycine, and Sorbitol. NaCl containing formulations showed the lowest sub-visible particle levels. These findings are further backed by DLS data and appearance data.
Figure 3:
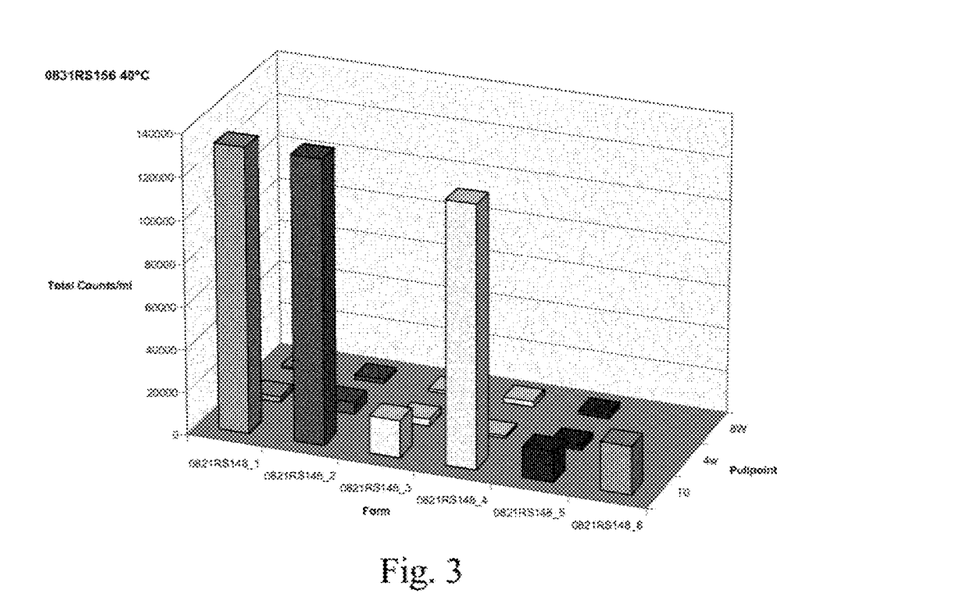
FIG. 3: Particle distribution of samples stored at 40° C. in the first tonifier screening experiment (example 1, "stressed storage conditions"), as determined with light obscuration Particle Counting, is shown. In general, sub-visible particle levels were highest at the initial time point. All formulations stored for 1 week and 2 weeks at 40° C. showed a significant decrease in sub-visible particle levels.

Results are shown in FIGS. 1, 2, and 3.

Example 3: Tonifier Screening 6 formulation development batches (no tonifier, Glycine, Mannitol, Sorbitol, NaCl) were compared. Batches comprising 15 mg hGH in aqueous solution (10.0 mg/ml, solution for injection 1.5 ml cartridge) have been stored for 24 months at 5° C.±3° C. ("intended storage 15 condition"), 3 months at 25° C.±2° C./60% relative humidity ("accelerated storage condition") and 2 weeks at 40° C.+2° C. ("stressed storage condition"). The different formulations are shown in table 5.

NaCl turned turbid or opalescent. After 2/3 months of storage at 5° C.±3° C. formulations containing Mannitol and Sorbitol turned progressively turbid/opalescent while formulation #0831RS156-5 containing NaCl stayed clear over the whole storage period. All these observations are further backed by particle counting and DLS data. Notably, all these 5 aggregation processes could not be monitored by SE-HPLC.

Figure 4:
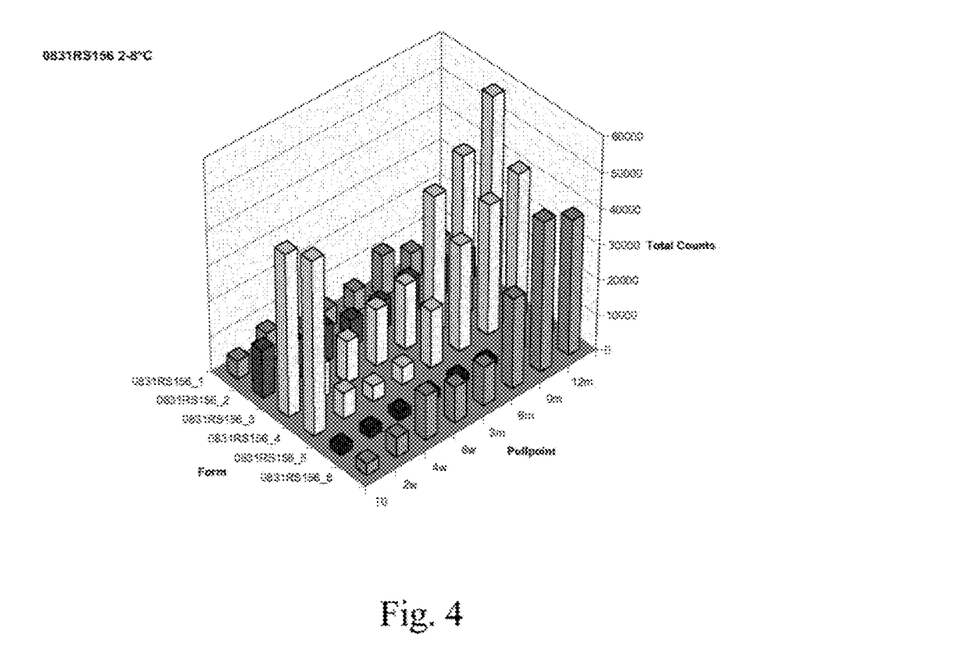
FIG. 4: Particle distribution of samples stored at 5° C. in the second tonifier screening 5 experiment (example 3, "intended storage condition"), as determined with light obscuration Particle Counting, is shown. In general, sub-visible particles progressively increased for formulations containing no tonifier and Glycine and were pronounced for formulations containing Sorbitol and Mannitol. NaCl containing formulations showed the lowest sub-visible particle levels. These findings are further backed by DLS data and appearance data.
Figure 5:
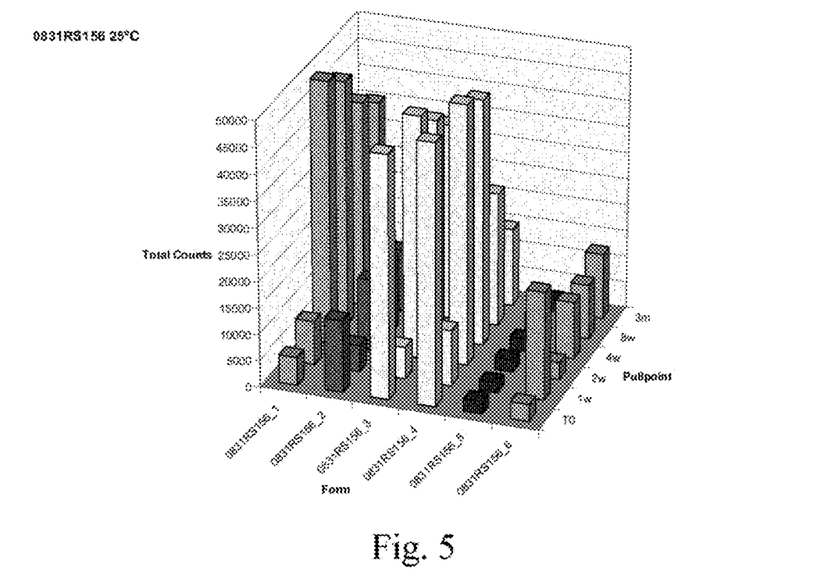
FIG. 5: Particle distribution of samples stored at 25° C. in the second tonifier screening experiment (example 3, "accelerated storage condition"), as determined with light obscuration Particle Counting, is shown. In general, sub-visible particles stayed at elevated levels for formulations containing no tonifier, Glycine, Sorbitol, and Mannitol. NaCl containing formulations showed the lowest sub-visible particle levels. These findings are further backed by DLS data and appearance data.
Figure 6:
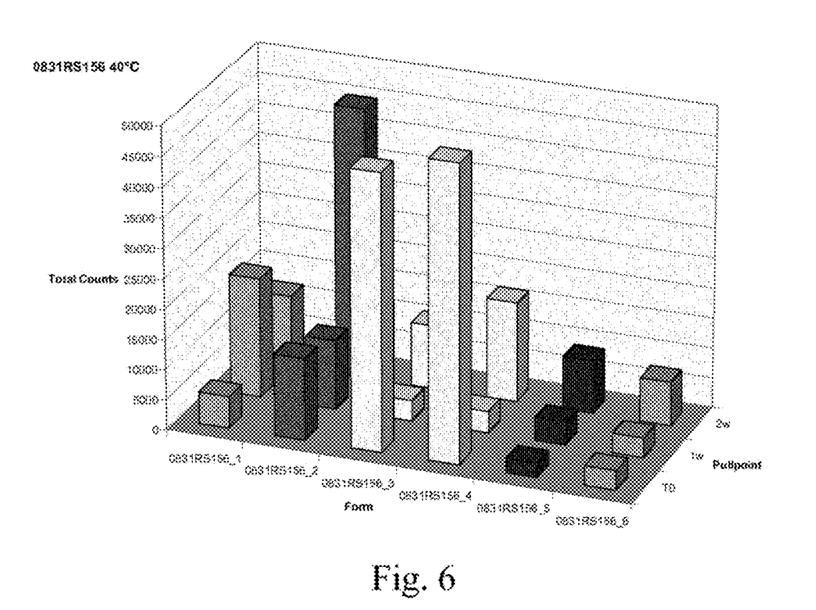
FIG. 6: Particle distribution of samples stored at 40° C. in the second tonifier screening experiment (example 3, "stressed storage condition"), as determined with light obscuration Particle Counting, is shown. In general, sub-visible particle levels were highest at the end of storage after 2 weeks at 40° C. Sub-visible particles were at elevated levels for formulations containing no tonifier, Glycine, Sorbitol, and Mannitol. NaCl containing formulations showed the lowest sub-visible particle levels. These findings are further backed by DLS data and appearance data.

At accelerated conditions a marginal increase in aggregation was observed by SE-HPLC. During storage at 25° C. all formulations except #083IRS 156-5 containing NaCl turned turbid or opalescent. At stressed conditions a slight increase in aggregation was observed by SE-10 HPLC. During storage at 40° C. all formulations are clear. Results are shown in FIGS. 4, 5, and 6.

Example 2: Optimization of Neutral Salt Concentration 8 formulation development batches (His/Mannitol, His/Phosphate/Mannitol, Arginine/Phosphate/Mannitol, Phosphate/Mannitol/0.41 mg/ml NaCl; Phosphate/Mannitol/3.5 mg/ml NaCl, Phosphate/7.07 mg/ml NaCl, Phosphate/Mannitol/14 mg/ml NaCl and Phosphate/0.41 mg/ml NaCl) were compared. Batches comprising 15 mg hGH in aqueous solution (10.0 mg/ml, solution for injection 1.5 ml cartridge) have been stored for 24 months at 5° C.±3° C. ("intended

TABLE 5

| | Formulation No | | | | | |
|---|---|---|---|---|---|---|
| | 0831RS156_1 | 0831RS156_2 | 0831RS156_3 | 0831RS156_4 | 0831RS156_5 | 0831RS156_6 |
| hGH | 10 mg/ml | 10 mg/ml | 10 mg/ml | 10 mg/ml | 10 mg/ml | 10 mg/ml |
| Phosphat | 10 mM | 10 mM | 10 mM | 10 mM | 10 mM | 10 mM |
| Glycin | | 18.17 mg/ml | | | | |
| Mannitol | | | 44.09 mg/ml | | | 44.09 |
| Sorbit | | | | 44.09 mg/ml | | |
| NaCl | | | | | 7.07 mg/ml | |
| Poloxamer 188 | 2 mg/ml | 2 mg/ml | 2 mg/ml | 2 mg/ml | 2 mg/ml | 3 mg/ml |
| Phenol | 3 mg/ml | 3 mg/ml | 3 mg/ml | 3 mg/ml | 3 mg/ml | 3 mg/ml |
| pH | 6.12 | 6.12 | 6.12 | 6.12 | 6.12 | 6.12 |
| water ad | 1 ml | 1 ml | 1 ml | 1 ml | 1 ml | 1 ml |
| tonicity | | 300 | 300 | 300 | 300 | 300 |

All tested batches appeared as a clear and colorless solution at the initial time point. During storage at 25° C. all formulations except #0831RS156-5 (table 5) containing storage condition") and 3 months at 25° C.+2° C./60% relative humidity ("accelerated condition"). The different formulations are shown in table 6.

TABLE 6

| | Formulation No | | | | | | | |
|---|---|---|---|---|---|---|---|---|
| | 835RS158_1 | 835RS158_2 | 835RS158_3 | 835RS158_4 | 835RS158_5 | 835RS158_6 | 835RS158_7 | 835RS158_8 |
| hGH | 10 mg/ml | 10 mg/ml | 10 mg/ml | 10 mg/ml | 10 mg/ml | 10 mg/ml | 10 mg/ml | 10 mg/ml |
| Phosphat | | 10 mM | 10 mM | 10 mM | 10 mM | 10 mM | 10 mM | 10 mM |
| Histidine | 1.13 | 1.13 mg/ml | | | | | | |
| Arginine | | | 1.03 mg/ml | | | | | |
| Mannitol | 38.7 | 38.7 mg/ml | 38.7 mg/ml | 42.85 mg/ml | 22.3 mg/ml | | | |
| NaCl | | | | 0.41 mg/ml | 3.5 mg/ml | 7.07 mg/ml | 14 mg/ml | 0.41 mg/ml |
| Poloxamer 188 | 3 mg/ml | 3 mg/ml | 3 mg/ml | 3 mg/ml | 3 mg/ml | 3 mg/ml | 3 mg/ml | 3 mg/ml |
| Phenol | 3 mg/ml | 3 mg/ml | 3 mg/ml | 3 mg/ml | 3 mg/ml | 3 mg/ml | 3 mg/ml | 3 mg/ml |
| pH | 6.12 | 6.12 | 6.12 | 6.12 | 6.12 | 6.12 | 6.12 | 6.12 |
| water ad | 1 ml | 1 ml | 1 ml | 1 ml | 1 ml | 1 ml | 1 ml | 1 ml |
| tonicity | 252 | 277 | 277 | 300 | 300 | 300 | 542 | 54.8 |

All tested batches appeared as a clear and colorless solution at the initial time point. During storage at 25° C. all formulations except #0835RS158-5, 6, and 7 containing 3.5 mg/ml, 7.07 mg/ml and 14 mg/ml NaCl turned turbid or opalescent.

After storage at 5° C.±3° C., formulations #0835RS158-5, 6. and 7 stayed clear while all other formulations turned progressively turbid/opalescent. All these observations are further backed by particle counting and DLS data. Notably, all these aggregation processes could not be monitored by SE-HPLC.

Figure 7:
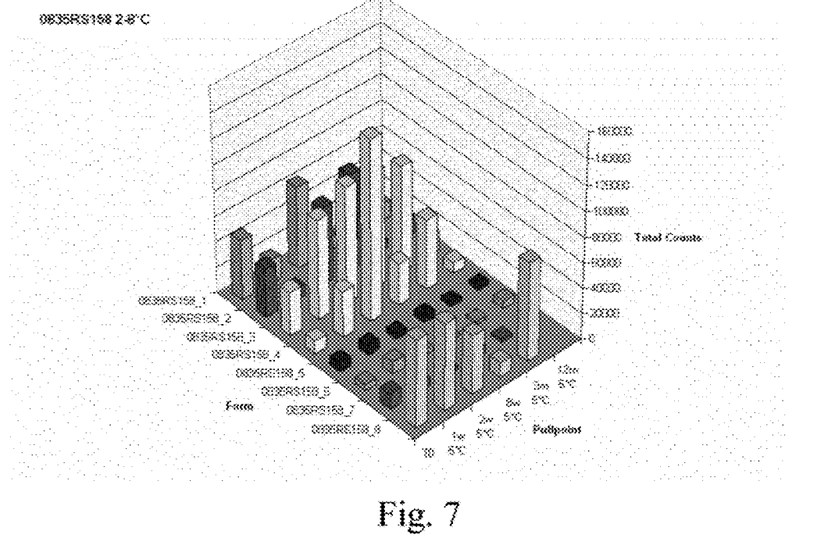
FIG. 7: Particle distribution of samples stored at 5° C. in the optimization of neutral salt concentration experiment (example 2, "intended storage condition"), as determined with light obscuration Particle Counting, is shown. Sub-visible particle levels were elevated for all batches, except for formulations containing 3.5 mg/ml, 7.07 mg/ml, and 14 mg/ml NaCl during storage at 5° C. This finding is further backed by DLS data (data not shown).
Figure 8:
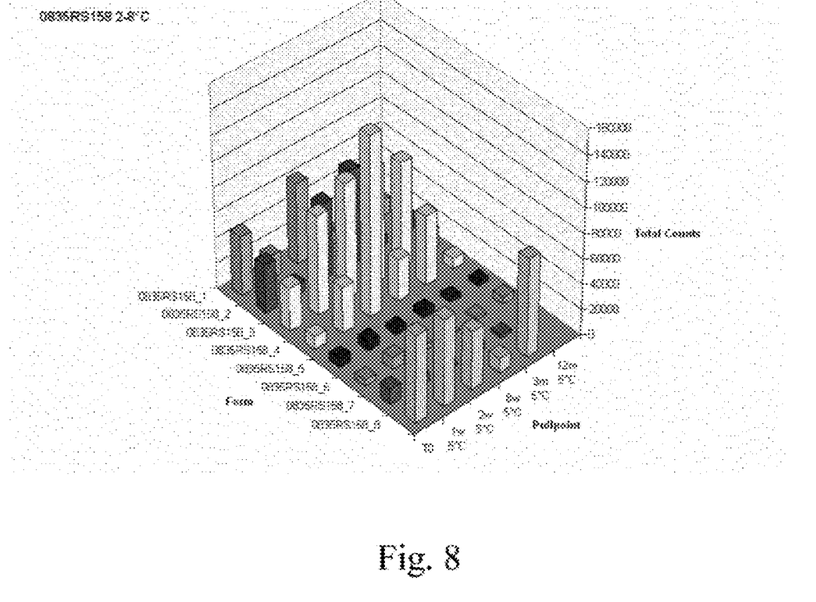
FIG. 8: Particle distribution of samples stored at 25° C. in the optimization of neutral salt concentration experiment (example 2, "accelerated condition"), as determined with light obscuration Particle Counting, is shown. Sub-visible particle levels were elevated for all batches except for formulations containing 3.5 mg/ml, 7.07 mg/ml, and 14 mg/ml NaCl during storage at 25° C. This finding is further backed by DLS data (data not shown).

At accelerated conditions a marginal increase in aggregation was observed by SE-HPLC. During storage at 25° C. all formulations except #0835RS158-5, 6, and 7 turned turbid or opalescent. Results are shown in FIGS. 7 and 8.

METHODS

Experimental methods are shown in the following tables and lists:

| Storage Conditions | Location |
|---|---|
| 5° C. ± 3° C. | Cold room B101/124 - intended storage |
| 25° C. ± 2° C./60% ± 5% relative humidity | Climate chamber B101/BPO/AL3 - accelerated storage |
| 40° C. ± 2° C. | Incubator B101/BPO/AL3 - stressed storage |

| Test | Analytical Method |
|---|---|
| Appearance content and container | Visual evaluation |
| pH | Potentiometric determination |
| Identity/Purity | nRPC (nanoflow reversed phase HPLC) |
| Product related impurities and substances/Content | SE HPLC (size exclusion HPLC) |
| Aggregation I | DLS (Dynamic Light scattering) |
| Aggregation II | light obscuration Particle Counting |
| Aggregation III (Only in example 2) | Microflow Imaging |

The invention claimed is:

1. A pharmaceutically acceptable aqueous formulation comprising a neutral salt, a phosphate buffer, a non-ionic surfactant, a preservative, and recombinant human growth hormone (hGH), wherein hGH is the only biopharmaceutical protein in the formulation, wherein the neutral salt is sodium chloride, and wherein the ratio of the concentration of recombinant hGH to the concentration of the neutral salt is from 1.2:1 to 2.0:1.

2. The formulation according to claim 1, wherein said non-ionic surfactant is selected from the group consisting of Poloxamer 188, Pluronic F-68, and Polysorbate 20.

3. The formulation according to claim 2, wherein said preservative is selected from the group consisting of phenol and benzyl alcohol.

4. The formulation according to claim 1, wherein said preservative is selected from the group consisting and benzyl alcohol.

5. The formulation according to claim 1, wherein recombinant hGH is present in a concentration ranging from 3 mg/mL to 20 mg/mL.

6. The formulation according to claim 1, wherein said neutral salt is present in a concentration ranging from 2 mg/mL to 20 mg/mL.

7. The formulation according to claim 1, wherein said ratio of the concentration of recombinant hGH to the concentration of the neutral salt is 1.4:1.

8. The formulation according to claim 1, wherein said neutral salt is the only neutral salt.

9. The formulation according to claim 1, wherein said non-ionic surfactant is Poloxamer 188 and said preservative is phenol.

10. The formulation according to claim 1, wherein said formulation consists of the neutral salt, the phosphate buffer, the non-ionic surfactant, the preservative, and the recombinant hGH.

11. A pharmaceutically acceptable aqueous formulation comprising:
  (a) sodium chloride in a concentration ranging from 2 mg/mL to 20 mg/mL;
  (b) a phosphate buffer;
  (c) a non-ionic surfactant selected from Poloxamer 188, Pluronic F-68, and Polysorbate 20 in a concentration ranging from 2 mg/mL to 3 mg/mL;
  (d) a preservative selected from phenol and benzyl alcohol in a concentration ranging from 0.11 mg/mL to 3 mg/mL; and
  (e) recombinant human growth hormone (hGH) in a concentration ranging from 2 mg/mL to 20 mg/mL,
  wherein the ratio of the concentration of recombinant hGH to the concentration of sodium chloride is of from 1.2:1 to 2.0:1, and
  wherein hGH is the only biopharmaceutical protein in the formulation.

12. The formulation according to claim 11, wherein said formulation consists of sodium chloride, the phosphate buffer, the non-ionic surfactant, the preservative, and the recombinant hGH.

13. The formulation according to claim 11, wherein sodium chloride is present in a concentration of 7 mg/mL.

14. The formulation according to claim 11, wherein said phosphate buffer is present in a concentration of 10 mM.

15. The formulation according to claim 11, wherein said non-ionic surfactant is present in a concentration of 3 mg/mL.

16. The formulation according to claim 11, wherein said preservative is present in a concentration of 3 mg/mL.

17. The formulation according to claim 11, wherein recombinant hGH is present in a concentration of 10 mg/mL.

18. A pharmaceutically acceptable aqueous formulation consisting of:
  (a) sodium chloride;
  (b) a phosphate buffer;
  (c) Poloxamer 188;
  (d) phenol; and
  (e) recombinant hGH,
  wherein the ratio of the concentration of recombinant hGH to the concentration of sodium chloride is from 1.2:1 to 2.0:1.

19. The formulation according to claim 18, wherein the ratio of the concentration of recombinant hGH to the concentration of sodium chloride is 1.4:1.

20. The formulation of claim 19, wherein sodium chloride is present in a concentration of 7 mg/mL, the phosphate buffer is present in a concentration of 10 mM, Poloxamer 188 is present in a concentration of 3 mg/mL, phenol is present in a concentration of 3 mg/mL, and recombinant hGH is present in a concentration of 10 mg/mL.

* * * * *